United States Patent
Nunley et al.

(10) Patent No.: US 9,987,051 B2
(45) Date of Patent: Jun. 5, 2018

(54) INTERBODY SPACER

(71) Applicant: K2M, Inc., Leesburg, VA (US)

(72) Inventors: Pierce Nunley, Shreveport, LA (US);
Stephanie Volk, Ashburn, VA (US);
Kaitlyn McClymont, Vienna, VA (US)

(73) Assignee: K2M, Inc., Leesburg, VA (US)

( * ) Notice: Subject to any disclaimer, the term of this patent is extended or adjusted under 35 U.S.C. 154(b) by 0 days. days.

(21) Appl. No.: 15/007,523

(22) Filed: Jan. 27, 2016

(65) Prior Publication Data

US 2016/0213486 A1 Jul. 28, 2016

Related U.S. Application Data (60) Provisional application No. 62/108,197, filed on Jan. 27, 2015, provisional application No. 62/196,371, filed on Jul. 24, 2015.

(51) Int. Cl.
*A61F 2/44* (2006.01)
*A61B 17/70* (2006.01)
(Continued)

(52) U.S. Cl.
CPC ...... *A61B 17/7059* (2013.01); *A61B 17/8625* (2013.01); *A61F 2/44* (2013.01);
(Continued)

(58) Field of Classification Search
CPC ............ A61F 2002/4475; A61F 2/4465; A61F 2002/30777; A61F 2002/30133;
(Continued)

(56) References Cited

U.S. PATENT DOCUMENTS 5,534,031 A 7/1996 Matsuzaki et al.
5,595,703 A 1/1997 Swaelens et al.
(Continued)

FOREIGN PATENT DOCUMENTS

DE 102008024281 A1 12/2009
DE 102008024288 A1 12/2009
(Continued)

OTHER PUBLICATIONS

Kim et al. Spinal Instrumentation Surgical Techniques, Thieme Medical publishers, 2004, pp. 232-245, 518-524, 532-537, 736-743, 795-800.
(Continued)

*Primary Examiner* — Eduardo C Robert
*Assistant Examiner* — Tara R Carter
(74) *Attorney, Agent, or Firm* — Carter, DeLuca, Farrell & Schmidt, LLP (57) ABSTRACT

An interbody spacer is disclosed and includes a body portion defining a longitudinal axis. The longitudinal axis includes a distal end portion, a proximal end portion, opposed side surfaces that extend between the distal and proximal end portions, and top and bottom surfaces configured and adapted to engage vertebral bodies. The body portion includes a cavity defined through the top and bottom surfaces that increases in width at a medial position thereof. The cavity is configured to retain biological material therein. A method of performing spinal surgery is also disclosed.

21 Claims, 3 Drawing Sheets

(51) Int. Cl.
*A61B 17/86* (2006.01)
*A61F 2/30* (2006.01)

(52) U.S. Cl.
CPC ............ *A61F 2/447* (2013.01); *A61F 2/4455* (2013.01); *A61F 2/4465* (2013.01); *A61F 2002/3092* (2013.01); *A61F 2002/3093* (2013.01); *A61F 2002/30622* (2013.01); *A61F 2002/30784* (2013.01); *A61F 2002/30904* (2013.01); *A61F 2002/4475* (2013.01); *A61F 2310/00023* (2013.01)

(58) Field of Classification Search
CPC .... A61F 2002/30224; A61F 2002/3023; A61F 2002/30112; A61F 2002/30125; A61F 2002/30123; A61F 2002/3013; A61F 2230/001
USPC ............................................ 623/17.11–17.16
See application file for complete search history.

(56) References Cited

U.S. PATENT DOCUMENTS

| | | | |
|---|---|---|---|
| 5,733,286 A | 3/1998 | Errico et al. | |
| 5,768,134 A | 6/1998 | Swaelens et al. | |
| 5,943,235 A | 8/1999 | Earl et al. | |
| 5,968,098 A | 10/1999 | Winslow | |
| 6,010,502 A | 1/2000 | Bagby | |
| 6,039,762 A | 3/2000 | McKay | |
| 6,143,033 A * | 11/2000 | Paul | A61F 2/28 623/16.11 |
| 6,245,108 B1 * | 6/2001 | Biscup | A61F 2/4455 606/246 |
| 6,391,058 B1 | 5/2002 | Kuslich et al. | |
| 6,409,765 B1 * | 6/2002 | Bianchi | A61B 17/1671 606/76 |
| 6,432,107 B1 | 8/2002 | Ferree | |
| 6,520,996 B1 | 2/2003 | Manasas et al. | |
| 6,530,955 B2 | 3/2003 | Boyle et al. | |
| 6,530,956 B1 | 3/2003 | Mansmann | |
| 6,716,247 B2 | 4/2004 | Michelson | |
| 6,758,849 B1 | 7/2004 | Michelson | |
| 7,018,416 B2 * | 3/2006 | Hanson | A61B 17/1671 623/17.16 |
| 7,238,206 B2 | 7/2007 | Lange et al. | |
| 7,509,183 B2 | 3/2009 | Lin et al. | |
| 7,665,979 B2 | 2/2010 | Heugel | |
| D623,749 S * | 9/2010 | Horton | D24/155 |
| 7,909,872 B2 | 3/2011 | Zipnick et al. | |
| 8,275,594 B2 | 9/2012 | Lin et al. | |
| 8,403,986 B2 | 3/2013 | Michelson | |
| 8,439,977 B2 | 5/2013 | Kostuik et al. | |
| 8,449,463 B2 | 5/2013 | Nunley et al. | |
| 8,449,585 B2 | 5/2013 | Wallenstein et al. | |
| 8,585,761 B2 | 11/2013 | Theofilos | |
| 8,590,157 B2 | 11/2013 | Kruth et al. | |
| 8,597,359 B2 * | 12/2013 | Butler | A61F 2/4465 623/17.11 |
| 8,673,011 B2 | 3/2014 | Theofilos et al. | |
| 8,697,231 B2 | 4/2014 | Longepied et al. | |
| 8,784,721 B2 | 7/2014 | Philippi et al. | |
| 8,801,791 B2 | 8/2014 | Soo et al. | |
| 8,814,919 B2 | 8/2014 | Barrus et al. | |
| 8,843,229 B2 | 9/2014 | Vanasse et al. | |
| 8,870,957 B2 | 10/2014 | Vraney et al. | |
| 8,903,533 B2 | 12/2014 | Eggers et al. | |
| 8,932,356 B2 | 1/2015 | Kraus | |
| 8,967,990 B2 | 3/2015 | Weidinger et al. | |
| 8,999,711 B2 | 4/2015 | Harlow et al. | |
| 9,011,982 B2 | 4/2015 | Muller et al. | |
| 9,283,078 B2 | 3/2016 | Roels et al. | |
| 2001/0047207 A1 | 11/2001 | Michelson | |
| 2001/0047208 A1 | 11/2001 | Michelson | |
| 2002/0120334 A1 * | 8/2002 | Crozet | A61B 17/86 623/17.11 |
| 2002/0128714 A1 | 9/2002 | Manasas et al. | |
| 2003/0040798 A1 | 2/2003 | Michelson | |
| 2003/0135276 A1 | 7/2003 | Eckman | |
| 2004/0024400 A1 | 2/2004 | Michelson | |
| 2004/0243237 A1 | 12/2004 | Unwin et al. | |
| 2004/0249471 A1 | 12/2004 | Bindseil et al. | |
| 2005/0021151 A1 | 1/2005 | Landis | |
| 2005/0149192 A1 | 7/2005 | Zucherman et al. | |
| 2005/0177238 A1 | 8/2005 | Khandkar et al. | |
| 2006/0247772 A1 * | 11/2006 | McKay | A61F 2/446 623/17.11 |
| 2007/0233272 A1 | 10/2007 | Boyce et al. | |
| 2008/0154379 A1 * | 6/2008 | Steiner | A61F 2/4455 623/17.16 |
| 2009/0093881 A1 | 4/2009 | Bandyopadhyay et al. | |
| 2009/0291308 A1 | 11/2009 | Pfister et al. | |
| 2010/0100131 A1 | 4/2010 | Wallenstein | |
| 2010/0137990 A1 | 6/2010 | Apatsidis et al. | |
| 2010/0228369 A1 | 9/2010 | Eggers et al. | |
| 2011/0144752 A1 | 6/2011 | Defelice et al. | |
| 2011/0165340 A1 | 7/2011 | Baumann | |
| 2011/0168091 A1 | 7/2011 | Baumann et al. | |
| 2011/0190904 A1 | 8/2011 | Lechmann et al. | |
| 2011/0301709 A1 | 12/2011 | Kraus et al. | |
| 2012/0046750 A1 | 2/2012 | Obrigkeit et al. | |
| 2012/0143334 A1 | 6/2012 | Boyce et al. | |
| 2012/0158062 A1 | 6/2012 | Nunley et al. | |
| 2012/0179261 A1 | 7/2012 | Soo | |
| 2012/0191188 A1 | 7/2012 | Huang | |
| 2012/0191189 A1 | 7/2012 | Huang | |
| 2012/0310364 A1 | 12/2012 | Li et al. | |
| 2013/0046345 A1 | 2/2013 | Jones et al. | |
| 2013/0116793 A1 | 5/2013 | Kloss | |
| 2013/0171019 A1 | 7/2013 | Gessler et al. | |
| 2013/0273131 A1 | 10/2013 | Frangov et al. | |
| 2014/0088716 A1 | 3/2014 | Zubok et al. | |
| 2014/0107785 A1 | 4/2014 | Geisler et al. | |
| 2014/0107786 A1 | 4/2014 | Geisler et al. | |
| 2014/0172111 A1 | 6/2014 | Lang et al. | |
| 2015/0018956 A1 | 1/2015 | Steinmann et al. | |
| 2015/0045924 A1 | 2/2015 | Cluckers et al. | |
| 2015/0134063 A1 | 5/2015 | Steinmann et al. | |
| 2015/0142158 A1 | 5/2015 | Szwedka | |
| 2015/0367575 A1 | 12/2015 | Roels et al. | |
| 2016/0058575 A1 | 3/2016 | Sutterlin, III et al. | |

FOREIGN PATENT DOCUMENTS

| | | |
|---|---|---|
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 1772108 B1 | 11/2015 |
| WO | 9000037 A1 | 1/1990 |
| WO | 9405235 A1 | 3/1994 |
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2011030017 A1 | 3/2011 |
| WO | 201317647 A1 | 2/2013 |
| WO | 2013155500 A1 | 10/2013 |

(56) References Cited

FOREIGN PATENT DOCUMENTS

WO 2013156545 A1 10/2013
WO 201496294 A1 6/2014

OTHER PUBLICATIONS

Fukuda, et al., Bone Ingrowth into Pores of Lotus Stem-Type Bioactive Titanium Implants Fabricated Using Rapid Prototyping Technique, Bioceramics Development and Applications, vol. 1 (2011), Article ID D110125, 3 pages.
Williams et al., CT Evaluation of Lumbar Interbody Fusion: Current Concepts, AJNR Am J Neuroradiol 26:2057-2066, Sep. 2005.
Cunningham et al, Design of Interbody Fusion Cages: Historical Considerations and Current Perspectives in Cage Technology; Surgical Techniques, Spinal Implants, pp. 421-465, 2006.
Akamaru et al., Healing of Autologous Bone in a Titanium Mesh Cage Used in Anterior Column Reconstruction After Total Spondylectomy; Spine vol. 27, No. 13, pp. E329-E333, 2002.
Lin et al., Interbody Fusion Cage Design Using Integrated Global Layout and Local Microstructure Topology Optimization; Spine, vol. 29, No. 16, pp. 1747-1754, 2004.
McAfee, Interbody Fusion Cages in Reconstructive Operations on the Spine, The Journal of Bone and Joint Surgery Incorporated, vol. 81A, No. 6, Jun. 1999, pp. 859-880.
Zdeblick, et al., LT-CAGE Lumbar Tapered Fusion Device Surgical Technique, Medtronic, pp. 1-25, 2000.
Kuslich, Lumbar Interbody Cage Fusion for Back Pain: An Update on the Bak (Bagby and Kuslich) System, Spine: State of the Art Reviews; vol. 13, No. 2, May 1999, pp. 295-311.
Cheung et al., Spinal Instrumentation Overview in Lumbar Degenerative Disorders: Cages, Lumbar Spine: Official Publication of the International Society for the Study of Lumbar Spine (3), pp. 286-291, 2004.
Sasso, Screws, Cages or Both?, <http://www.spineuniverse.com/professional/technology/surgical/thoracic/>, pp. 1-11, Sep. 2012.
Costa et al., Stand-alone cage for posterior lumbar interbody fusion in the treatment of high-degree degenerative disc disease: design of a new device for an "old" technique. A prospective study on a series of 116 patients, Eur Spine J. May 2011: 20 (Suppl 1), pp. 46-56.
Lin, et al. Structural and mechanical evaluations of a topology optimized titanium interbody fusion cage fabricated by selective laser melting process, Journal of Biomedical Materials Research Part A DOI 10.1002/jbm.a, pp. 272-279, Apr. 2007.
Chong et al., The design evolution of interbody cages in anterior cervical discectomy and fusion: a systematic review; BMC Musculoskeletal Disorders 2015 16:99, pp. 1-20.
Bridwell et al.., Specialty Update, What's New in Spine Surgery, The Journal of Bone and Joint Surgery, Incorporated, pp. 1022-1030, Core 1st page of article, 2015.
EBI Spine, Promotional flyer, 1 page 2005.
Synthes Contact Fusion Cage, Technique Guide, 2007, pp. 1-16.
Stryker, Ttritanium basic science summary, technical monograph, pp. 1-2, 2016.
Sofamar Danek Interim Thread Fusion Device, pp. 32-45, 1999.

\* cited by examiner

INTERBODY SPACER

CROSS-REFERENCE TO RELATED APPLICATIONS

This application claims priority to, and the benefit of, U.S. Provisional Patent Application Ser. No. 62/108,197, filed on Jan. 27, 2015 and U.S. Provisional Patent Application Ser. No. 62/196,371, filed on Jul. 24, 2015. The entire contents of each of these prior applications are hereby incorporated by reference herein.

BACKGROUND

Technical Field

The present disclosure relates to an apparatus for treating spinal conditions, and more particularly, to an intervertebral implant and a method of use therefor.

Background of Related Art

The human spinal column is a highly complex structure. It includes twenty-four discrete bones, known as vertebrae, coupled sequentially to one another to house and protect critical elements of the nervous system. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina.

The vertebrae are separated and cushioned by thin pads of tough, resilient fiber known as inter-vertebral discs. Inter-vertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

For many reasons, such as aging and trauma, the intervertebral discs can begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. After a partial or complete discectomy, the normally occupied space between adjacent vertebral bodies is subject to collapse and/or misalignment due to the absence of all or part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged and moved from their desired implantation location due to movement by the patient before sufficient bone growth has occurred.

Bone growth is a key factor in ensuring adequate retention of the implant to the vertebra. Specifically, bone ingrowth within and around the prosthetic implant promotes fusion between the adjacent vertebra, thereby strengthening the joint therebetween. However, conventional implants do not allow optimal space for bone ingrowth. In these instances, as the prosthetic implants do not mimic bone density of the adjacent vertebra, the body rejects the implant, and non-union (i.e., no fusion) occurs.

Conventional prosthetic implants are typically constructed in a manner that inhibits bone ingrowth, particularly those that include no spaces or avenues for such bone growth to occur within and around the prosthetic implant. The lack of fusion may allow the implant to become dislodged or moved from its desired location. Additionally, in the instances where the prosthetic implant includes a lumen for the packing of ingrowth material, the material is often able to dislodge from the lumen, and in some instances, from the implant, thereby reducing the chances that adequate bone ingrowth occurs.

Therefore, a need exists for a prosthetic implant that can mimic the density of bone or adequately retain ingrowth material therein to allow for optimal bone ingrowth and provide a solid fusion of the vertebral segments.

SUMMARY

In accordance with an embodiment of the present disclosure, there is provided an interbody spacer including a body portion defining a longitudinal axis. The body portion includes a distal end portion, a proximal end portion, opposed side surfaces that extend between the distal and proximal end portions, and top and bottom surfaces configured and adapted to engage adjacent vertebral bodies. The body portion includes a cavity defined between the top and bottom surfaces that increases in width at a medial position thereof and is configured to retain biological material therein.

In embodiments, the cavity may include undercuts defined therein where the undercuts define convex sidewalls. Alternatively, the undercuts may define planar sidewalls.

In embodiments, one of the top or bottom surfaces may include a plurality of substantially concentrically arranged ridges. The plurality of substantially concentrically arranged ridges may include a plurality of ring-shaped protrusions that defines a generally saw-tooth pattern in a radial direction. The plurality of concentrically arranged ridges may include a cross-hatched pattern defined therein adjacent the opposed side surfaces of the body portion.

In embodiments, the proximal end portion may define a recess configured and adapted to engage an implant insertion device. The proximal end portion may have a convex surface adapted to engage an implant insertion device. The convex surface of the proximal end portion may define a threaded aperture aligned with the longitudinal axis of the body portion and adapted to threadably engage an implant insertion device.

In embodiments, the distal end portion may include a substantially contoured configuration. The top and bottom surfaces of the body portion may approximate towards one another along the longitudinal axis adjacent the distal portion.

In embodiments, the top and bottom surfaces may be substantially parallel. The top and bottom surfaces may approximate towards one another in a direction transverse to the longitudinal axis.

In accordance with an embodiment of the present disclosure, a method of performing spinal surgery is disclosed. The method includes preparing an intervertebral space between first and second vertebral bodies and advancing an interbody spacer into the intervertebral space. The interbody spacer includes a body portion defining a longitudinal axis and includes a distal end portion, a proximal end portion, opposed side surfaces that extend between the distal and proximal end portions, and top and bottom surfaces configured and adapted to engage adjacent vertebral bodies, wherein the body portion includes a cavity defined through the top and bottom surfaces, the cavity increasing in width at a medial position thereof and configured to retain biological material therein.

In embodiments, the method may include packing the cavity with bone in-growth material. The method may include packing the cavity with drugs.

In embodiments, advancing the interbody spacer may include the interbody spacer having a cavity that includes undercuts defined therein. The undercuts may define convex sidewalls. The undercuts may define planar sidewalls.

In embodiments, advancing the interbody spacer may include the interbody spacer having a plurality of substantially concentrically arranged ridges. The plurality of substantially concentrically arranged ridges may include a plurality of ring-shaped protrusions that define a generally saw-tooth pattern in a radial direction.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure are now described in detail with reference to the drawings in which like reference numerals designate identical or corresponding elements in each of the several views. As commonly known, the term "clinician" refers to a doctor, a nurse, or any other care provider and may include support personnel. Additionally, the term "proximal" refers to the portion of the device or component thereof that is closer to the clinician and the term "distal" refers to the portion of the device or component thereof that is farther from the clinician. In addition, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 1:
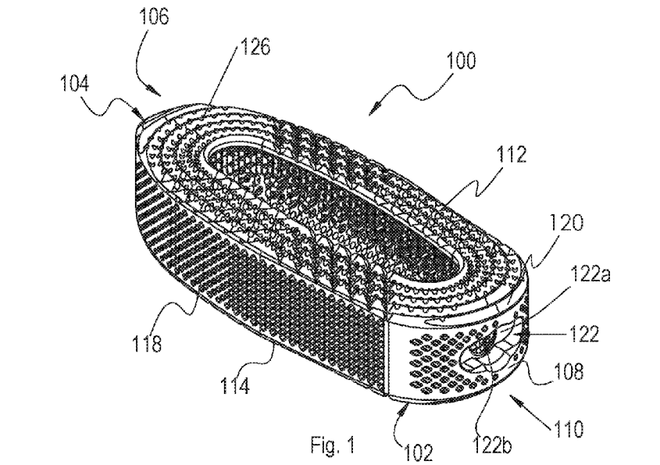
FIG. 1 is rear, perspective view, of an interbody spacer provided in accordance with the present disclosure.
Figure 2:
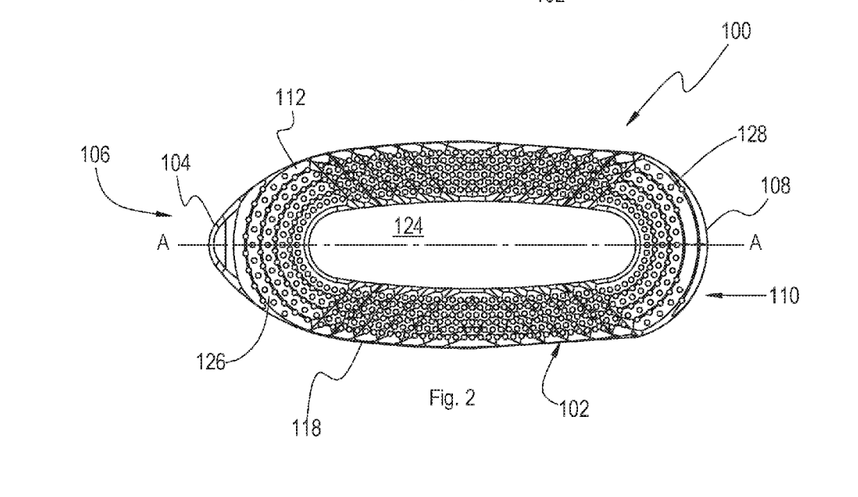
FIG. 2 is a top, plan view, of the interbody spacer of FIG. 1.
Figure 4:
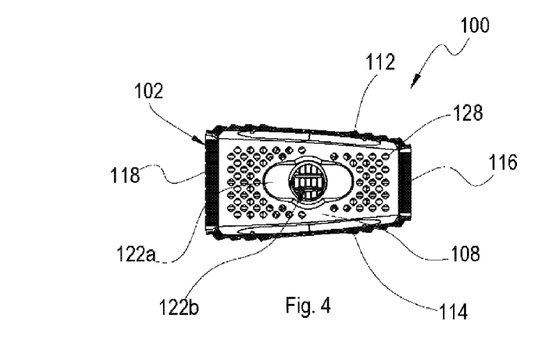
FIG. 4 is a rear view of the interbody spacer of FIG. 1.

Referring now to the drawings, FIGS. 1-5B illustrate one embodiment of an interbody spacer provided in accordance with the present disclosure generally identified by reference numeral 100. Interbody spacer 100 includes a body portion 102 illustrated as having a generally torpedo shape (FIG. 1); however, it is contemplated that body portion 102 may include any suitable shape such as square, rectangular, circular, oval, or the like. As best illustrated in FIG. 2, body portion 102 includes a substantially contoured first end surface 104, at a distal or leading end 106, and a second end surface 108 opposite thereto at a proximal or trailing end 110, having a rounded configuration. First end surface 104 defines axis A-A and extending through an apex thereof and through an apex of second end surface 108, thereby bisecting first and second end surfaces 104, 108. Body portion 102 extends between first and second end surfaces 104, 108 to define respective top and bottom surfaces 112 and 114 (FIG. 3), respectively, as well as opposed side surfaces 116, 118 (FIG. 2). As best illustrated in FIG. 4, top surface 112 is shown as approximating bottom surface 114 in a direction from side surface 116 towards side surface 118, although it is contemplated that top and bottom surfaces 112, 114 may be substantially planar relative to one another, approximate in a direction from side surface 118 towards side surface 116, approximate in a distal direction, approximate in a proximal direction, or any combination thereof. Additionally, top and bottom surfaces 112, 114 are illustrated as being substantially planar, although other configurations are also contemplated such as convex, concave, or the like. Top and bottom surfaces 112, 114 approximate at distal end 106 along longitudinal axis A-A (FIG. 3) in order to facilitate insertion within the intervertebral space and enhance the atraumatic character of body portion 102. In this manner, the intersection of top and bottom surfaces 112, 114 with each of the first and second end surfaces 104, 108 and opposed side surfaces 116, 118 may include a fillet or rounded configuration 120 to inhibit sharp edges from causing trauma to the surrounding tissue and/or vertebral bodies.

As best illustrated in FIG. 2, opposed side surfaces 116, 118 include a generally convex profile, each extending in an anterior and posterior direction, respectively. As can be appreciated, opposed side surfaces may include a concave profile, a planar profile, or any combination thereof. In embodiments, side surface 116 may include a different profile than that of side surface 118.

With reference to FIGS. 1 and 4, second end surface 108 includes a recess 122 defined therethrough extending along longitudinal axis A-A and terminating in a distal face 122a. A threaded aperture 122b is defined through distal face 122a and extends through an interior wall of body portion 102 along longitudinal axis A-A as will be described in further detail hereinbelow. Threaded aperture 122a and recess 122 cooperate to releasably engage a suitable insertion tool, such as that described in U.S. Patent Application Serial No. 2012/0158062, filed Oct. 11, 2011, the entire contents of which are hereby incorporated by reference herein. Although illustrated as having a generally oval shape with a circular cutout, recess 122 may include any suitable shape suitable capable of engaging a suitable insertion instrument, such as square, rectangular, hexagonal, or the like.

Figure 3:
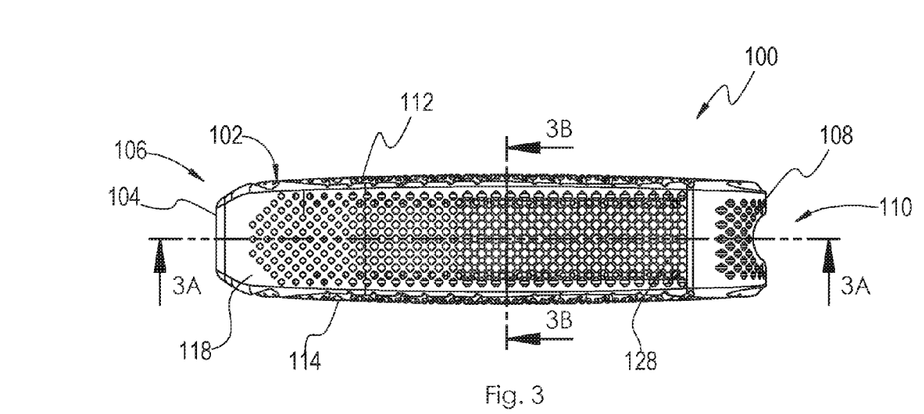
FIG. 3 is a side, elevation view, of the interbody spacer of FIG. 1.
Figure 3A:
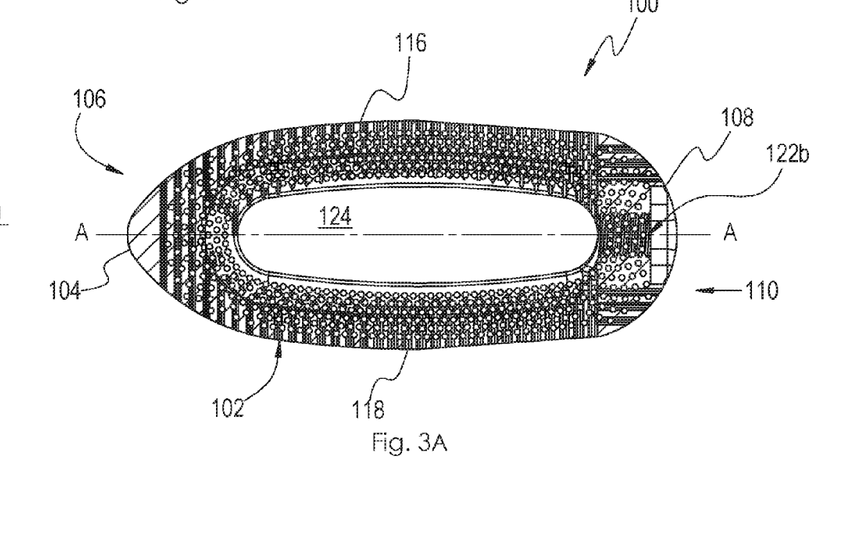
FIG. 3A is a cross-sectional view of the interbody spacer of FIG. 3, taken along line 3A-3A.
Figure 3B:
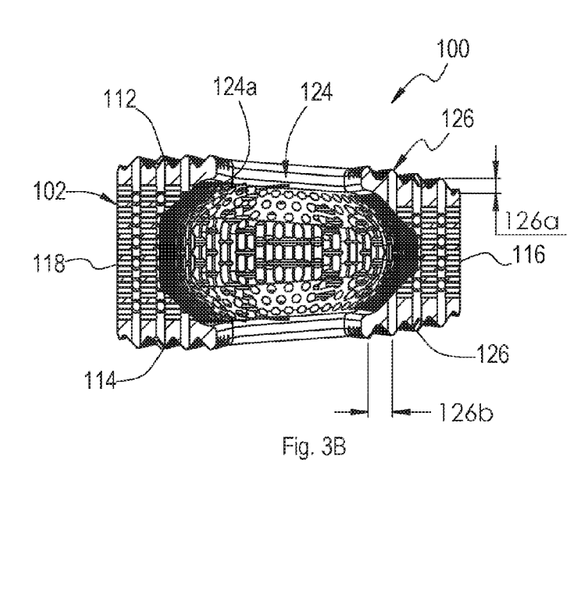
FIG. 3B is a cross-sectional view of the interbody spacer of FIG. 3, taken along line 3B-3B.

Body portion 102 includes a through-bore or cavity 124 defined through top and bottom surfaces 112, 114. Although shown as having a configuration similar to that of the overall outer profile of body portion 102, it is contemplated that through-bore 124 may have any suitable shape, such as square, rectangular, circular, or the like. As best illustrated in FIG. 3B, through-bore 124 includes an undercut defining convex side walls 124a such that the interior volume of through-bore 124 increases about longitudinal axis A-A (i.e., the medial portion of body portion 102). As can be appreciated, the convex side walls 124a may extend along the circumference of through-bore 124. In this manner, through-bore 124 is configured to receive a greater amount of biological material than is possible with a through-bore having planar side walls. In embodiments, through-bore 124 may include any suitable cross-section when viewed along a plane extending vertically and/or horizontally from longitudinal axis A-A, such as a trapezoid, ovoid, spheroid, cuboid, or the like. In one non-limiting embodiment, through-bore 124 includes upper and lower undercuts 124b and 124c, respectively (FIG. 5B), defining a generally trapezoidal profile. It is contemplated that through-bore 124 may receive a biological material such as allograft material, autograft material, calcium phosphate/bone marrow aspirate (BMA), autogenous material, synthetic materials comprised of a biocompatible, osteoconductive, osteoinductive, or osteogeneic material such as VITOSS® Synthetic Cancellous Bone Void Filler material, or any other suitable biological material known in the art. The convex side walls 124a and undercuts 124b, 124c aid in retaining the bone growth material therein, reducing the possibility that the biological material may separate or become dislodged from interbody spacer 100. Through-bore 124 includes a cross-sectional area or surface area that is greater than any orifice of the plurality of orifices or enlarged orifices detailed hereinbelow. In embodiments, through-bore 124 includes a surface area that is equal to or greater than 25% of the surface area of top surface 112 or bottom surface 114.

Top and bottom surfaces 112, 114 of body portion 102 are configured to engage respective endplates of adjacent vertebral bodies. In this manner, a plurality of ridges or projections 126 (FIGS. 1 and 2) is disposed on each of top and surfaces 112, 114 to aid in securing interbody spacer 100 to each respective adjacent vertebral body and stability against fore and aft, oblique or side to side movement of interbody spacer 100 within the intervertebral space. Specifically, the plurality of ridges 126 are arranged in a generally ring-shaped orientation and define a generally saw-tooth pattern extending radially outward. Each of the plurality of ridges 126 are arranged concentrically with through-bore 124, although other configurations are also contemplated, such as eccentric in a distal direction, proximal direction, either lateral direction, or any combination thereof. In embodiments, each ridge of the plurality of ridges 126 includes a height 126a of about 0.030 inches and a width 126b of about 0.062 inches with a crest-to-crest angle of 80-degrees (FIG. 3B). As best illustrated in FIG. 5, the plurality of ridges 126 may include a cross-hatched or crenellated pattern 126a defined therein adjacent each of opposed side surfaces 116, 118 to further aid in securing interbody spacer 100 to each respective vertebral body, although other suitable patterns are also contemplated.

Interbody spacer 100 is constructed of a biocompatible material, such as commercially pure titanium and includes a porosity capable of promoting bone ingrowth and fusion with vertebral plate 100. In this manner, top and bottom surfaces 112, 114 and opposed side surfaces 116, 118 have a surface roughness that can promote bone growth and fusion with interbody spacer 100. The surface roughness may be in a range of about 0.10-50 μm, and preferably in a range of about 3-4 μm. As can be appreciated, top and bottom surfaces 112, 114 and opposed side surfaces 116, 118 may include the same or different surface roughness's (i.e., the surface roughness of top surface 112 may be different than the surface roughness of bottom surface 114), or top and bottom surfaces 112, 114 and opposed side surfaces 116, 118 may not include a surface roughness; rather, top and bottom surfaces 112, 114 and opposed side surfaces 116, 118 may be smooth. In embodiments top and bottom surfaces 112, 114 and opposed side surfaces 116, 118 may include any combination of surface roughness or smooth surface. Additionally, a plurality of orifices 128 is defined therethrough configured to promote bone ingrowth. The plurality of orifices 128 is defined through each of first and second end surfaces 104, 108, top and bottom surfaces 112, 114, opposed side surfaces 116, 118 and may include any suitable cross-section such as circular, oval, square, hexagonal, rectangular, diamond, or the like. As can be appreciated, the plurality of orifices 128 defined through each of top and bottom surfaces 112, 114, opposed side surfaces 116, 118, and first and second end surfaces 104, 108 may include the same cross-section or different cross section, or combinations thereof (i.e., an intermixing of circular and diamond cross-sections on the same surface or different surfaces). In one non-limiting embodiment, the plurality of orifices 128 defined through top and bottom surfaces 112, 114 include a circular cross-section, whereas the plurality of orifices 128 defined through each of opposed side surfaces 116, 118 and first and second end surfaces 104, 108 include a generally diamond shaped cross-section. The plurality of orifices 128 defined through top and bottom surfaces 112, 114 are oriented in a direction normal to a plane extending horizontally to longitudinal axis A-A. The plurality of orifices 128 defined through opposed side surfaces 116, 118 are oriented in a direction normal to a plane extending vertically through longitudinal axis A-A, and the plurality of orifices 128 defined through first and second end surfaces 104, 108 are oriented along longitudinal axis A-A. However, it is contemplated that the plurality of orifices 128 may be oriented in any direction relative to longitudinal axis A-A.

The plurality of orifices 128 mimic bone growth along Haversian canals and lamellar structures of bone. In this manner, the plurality of orifices 128 pass entirely through top and bottom surfaces 112, 114, opposed side surfaces 116, 118, and first and second end surfaces 104, 108. Alternatively, the plurality of orifices 128 may be offset in relation to one another. In this manner, an orifice 128 defined through bottom surface 114 will be offset from a corresponding orifice 128 defined through top surface 112. In embodiments, orifices 128 may be defined through top and bottom surfaces 112, 114, opposed side surfaces 116, 118, and/or first and second end surfaces 104, 108 normal thereto or at angles relative thereto. In one non-limiting embodiment, orifices 128 are defined through top and bottom surfaces 112, 114 at angles incident relative to each other, thereby forming a chevron configuration. As can be appreciated, each of the orifices 128 formed through top and bottom surfaces 112, 114 and opposed side surfaces 116, 118, respectively, form a respective channel therebetween, thereby interconnecting an orifice formed through top surface 112 and an orifice formed through bottom surface 114, or an orifice formed through side surface 116 and an orifice formed through side surface 118. It is contemplated that the density of orifices 128 may be different on each of top and bottom surfaces 112, 114, opposed side surfaces 116, 118, and first and second end surfaces 104, 108, respectively, or may increase or decrease in density at various location thereon. The plurality of orifices include a diameter in a range of about 50-1000 μm, although a diameter between 300-700 μm is preferable. As can be appreciated, for shapes other than circular, orifices 128 include a cross-sectional area in a range of about 0.0019 μm$^2$-0.785 μm$^2$, although a cross-sectional area between 0.0707 μm$^2$-0.385 μm$^2$ is preferable. As can be appreciated, the plurality of orifices 128 may include orifices 128 having varying sizes and shapes relative to each other. The plurality of orifices 128 reduce the density and stiffness of interbody spacer 100 to enable the application of bone putty or the like (e.g., bone morphogenetic proteins) to interbody spacer 100 to promote bone ingrowth and fusion of adjacent vertebral bodies secured to interbody spacer 100. Bone ingrowth and fusion strengthen interbody spacer 100, thereby reducing the probability that interbody spacer 100 would fracture and the likelihood that micromotion would occur would likewise be reduced. Alternatively, it is contemplated that interbody spacer 100 be constructed without orifices 128 defined therethrough, but rather using a solid construction (FIGS. 5, 5A, and 5B).

Figure 5:
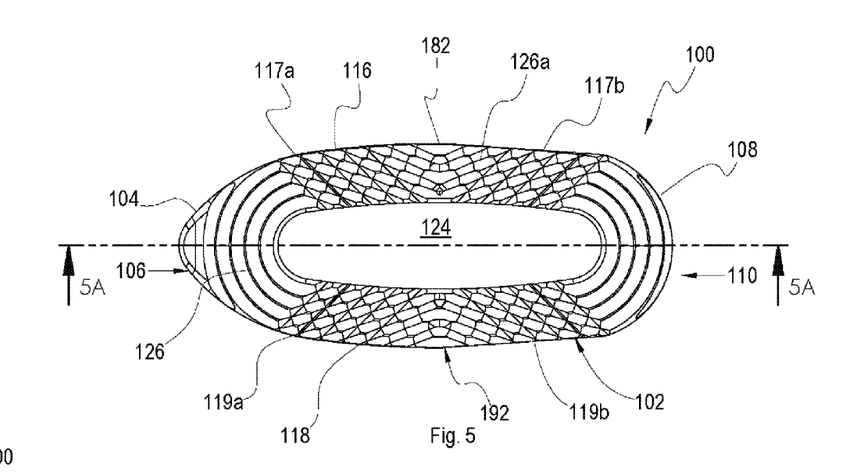
FIG. 5 is a top, plan view, of another embodiment of an interbody spacer provided in accordance with the present disclosure.
Figure 5A:
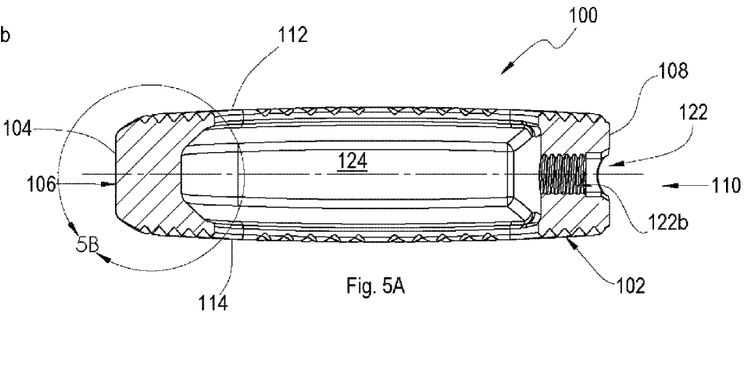
FIG. 5A is a cross-sectional view of the interbody spacer of FIG. 5, taken along line 5A-5A.
Figure 5B:
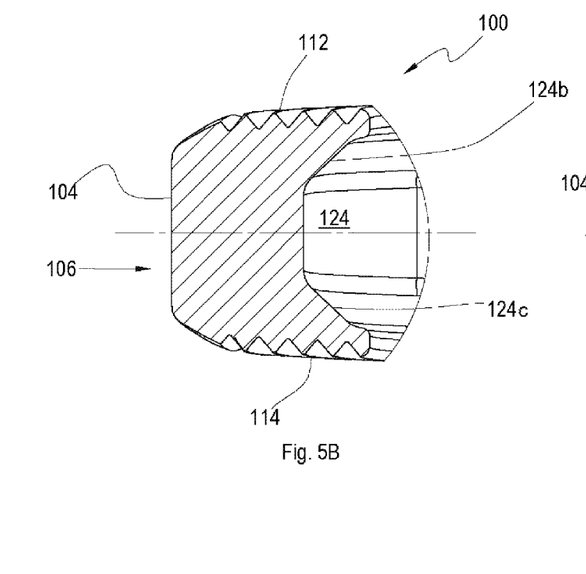
FIG. 5B is an enlarged view of the area of detail indicated in FIG. 5A.

Further still, with continued reference to FIG. 5, opposed side surfaces 116, 118 include transition portions 182, 192 respectively. Transition portions 182, 192 bisect opposed side surfaces 116, 118 into first and second sloped portions 117a, 117b for side surface 116 and first and second sloped portions 119a, 119b for side surface 118. First sloped portion 117a extends between first end surface 104 and transition portion 182 while second sloped portion 117b extends between transition portion 182 and second end surface 106. Similarly, first sloped portion 119a extends between first end surface 104 and transition portion 192 while second sloped portion 119b extends between transition portion 192 and second end surface 106. Each of first and second sloped portions 117a, 117b, 119a, 119b defines a slope having a liner (i.e., non-curvate) surface. Each of the first and second sloped portions 117a, 117b, 119a, 119b defines an acute angle with respect to the central longitudinal axis A-A of interbody spacer 100. In addition, transition portions 182, 192 may be a point or a plane. Transition portions 182, 192 bisect interbody spacer 100 between first and second end surfaces 104, 106.

As can be appreciated, manufacturing interbody spacer 100 using standard machining methods (e.g., lathe, mill, EDM, etc.) could be difficult. In view of this, it is contemplated that in addition to manufacturing interbody spacer 100 using the aforementioned conventional means, interbody spacer 100 may be manufactured by means of additive manufacturing methods (e.g., SDM, SLPP, DMLS (i.e., EOS), SLS, SLM, SHS, EBM, VAT photopolymerisation, material jetting, binder jetting, or the like). In one non-limiting embodiment, interbody spacer 100 is may be manufactured using Selective Laser Powder Processing (SLPP). SLPP utilizes powdered metal and a laser which sinters or cures the metal in a selective fashion according to the design intent in thin layers. In embodiments, the layers have a thickness of about 250 Interbody spacer 100 is built layer by layer to allow for more design options and features that would be difficult to be machined using conventional methods. Specifically, a first layer of powder is applied to a specialized build plate, at which point the laser cures portions of the powder according to the design intent. At this point, a second layer is applied to the build plate and the laser is again used to cure selective portions of this second layer. This process is repeated until interbody spacer 100 is fully formed. Once interbody spacer 100 is fully formed, uncured powder is removed using compressed air or other similar means. Next, post machining is performed on interbody spacer 100 to remove any burrs or similar imperfections embedded within interbody spacer 100 during the additive manufacturing process. In embodiments, the burrs are removed by means of buffer wheels, clippers, files, or the like. Once de-burred, interbody spacer 100 is heat treated, and thereafter, media blasted using aluminum oxide. Thereafter, interbody spacer 100 is immersed in a hydrofluoric bath to strip the aluminum oxide therefrom. Finally, interbody spacer 100 is inspected by quality control personnel (or using automated means), cleaned via ultrasonic cleaning, dried, and packaged. It is contemplated that the design of interbody spacer 100 may be customized for each specific patient using SLPP. For a detailed description of exemplary manufacturing methods, reference may be made to U.S. Pat. No. 8,590,157, issued on Nov. 26, 2013 to Kruth et al., the entire contents of which are hereby incorporated by reference herein.

Interbody spacer 100 may be constructed from commercially pure titanium, titanium alloy, cobalt-chrome, ceramic, polyetheretherketone (PEEK), or any other suitable biocompatible material. In embodiments, interbody spacer 100 may be manufactured using a three-dimensional printer utilizing a biocompatible polymer.

With reference to FIGS. 1-5B, in use, an intervertebral space if first prepared, e.g., damaged or diseased tissue is removed. Thereafter, an appropriately sized interbody spacer 100 is selected based on the patient's spinal characteristics and the desired amount of lordosis. Next, the interior space of throughbore 124 of body portion 102 may be packed with bone in-growth material, drugs, or other suitable materials or compounds. Examples of such materials are allograft material, or synthetic materials comprised of a biocompatible, osteoconductive, osteoinductive, or osteogeneic material such as VITOSS® Synthetic Cancellous Bone Void Filler material. Next, a suitable insertion instrument (not shown) is advanced within recess 122 and threaded into threaded aperture 122a of body portion 102 until interbody spacer 100 is securely affixed to the insertion instrument. At this point, interbody spacer 100 is advanced within an incision within the patient, and thereafter, the previously prepared intervertebral space of the patient's spine. Once interbody spacer 100 is placed within the intervertebral space such that interbody spacer 100 rests on the distal apophyseal ring of the vertebral body, the tool (not shown) is released from threaded aperture 124a and removed from recess 124, and thereafter, the incision within the patient. By residing on the apophyseal ring, interbody spacer 100 is less likely to experience subsidence into the end plates which will facilitate fusion between the intervertebral plates. The interbody spacer disclosed herein is suitable for use in the procedure described in U.S. Pat. No. 8,449,463, issued May 28, 2013 to Nunley et al., the entire contents of which are hereby incorporated by reference herein.

This process may be repeated as many times as the procedure requires, whether it be for the same interbody spacer 100 or for a plurality of interbody spacers 100 as required by the procedure being performed.

It is envisioned that the manufacturing processes and orifice designs detailed above may be utilized to form various other medical devices known in the art. In this manner, the additive manufacturing process detailed above may be employed to form corpectomy devices, fixed spinal implants, expandable spinal implants, bone screws, cervical implants, and the like. Similarly, the orifice designs detailed above may be formed in any of the beforementioned medical devices that would benefit from an increased ability to fuse with bone. Examples of such devices may be found in the following commonly owned references: U.S. Pat. No. 8,585,761 to Theofilos, U.S. Pat. No. 8,673,011 to Theofilos et al., U.S. application Ser. No. 14/936,911 to Sutterlin et al., U.S. Pat. No. 8,801,791 to Soo et al., U.S. Pat. No. 8,439,977 to Kostuik et al., U.S. Patent Application Publication No. 2010/0100131 to Wallenstein, U.S. Patent Application Publication No. 2012/0179261 to Soo, U.S. Pat. No. 8,449,585 to Wallenstein et al., U.S. Pat. No. 8,814,919 to Barrus et al., U.S. Pat. No. 5,733,286 to Errico et al., and U.S. Patent Application Publication No. 2013/0046345 to Jones et al.

It will be understood that various modifications may be made to the embodiments of the presently disclosed interbody spacer. Therefore, the above description should not be construed as limiting, but merely as exemplifications of embodiments. Those skilled in the art will envision other modifications within the scope and spirit of the present disclosure.

What is claimed is:

1. An interbody spacer comprising:
a body portion defining a longitudinal axis, the body portion including a distal end portion, a proximal end portion, opposed side surfaces that extend between the distal and proximal end portions, and top and bottom surfaces defining a vertical axis therethrough, at least one of the top and bottom surfaces having projections thereon configured and adapted to engage adjacent vertebral bodies, wherein the body portion includes a cavity defined between the top and bottom surfaces and bounded by the opposed side surfaces and the distal and proximal end portions, the cavity defining sidewalls having a concave profile extending along the vertical axis, the concave profile extending contiguously along a perimeter of the cavity, wherein the cavity is configured to retain biological material therein.

2. The interbody spacer according to claim 1, wherein the cavity includes undercuts defined therein, the undercuts defining convex sidewalls forming a portion of the sidewalls of the cavity.

3. The interbody spacer according to claim 1, wherein the cavity includes undercuts defined therein, the undercuts defining planar sidewalls forming a portion of the sidewalls of the cavity.

4. The interbody spacer according to claim 1, wherein one of the top or bottom surfaces includes a plurality of substantially concentrically arranged ridges.

5. The interbody spacer according to claim 4, wherein the plurality of concentrically arranged ridges is a plurality of ring-shaped protrusions that defines a generally saw-tooth pattern in a radial direction.

6. The interbody spacer according to claim 5, wherein the plurality of concentrically arranged ridges includes a cross-hatched pattern defined therein adjacent the opposed side surfaces of the body portion.

7. The interbody spacer according to claim 1, wherein the proximal end portion defines a recess configured and adapted to engage an implant insertion device.

8. The interbody spacer according to claim 7, wherein the proximal end portion has a convex surface adapted to engage an implant insertion device.

9. The interbody spacer according to claim 8, wherein the convex surface of the proximal end portion defines a threaded aperture aligned with the longitudinal axis of the body portion, the threaded aperture adapted to threadably engage an implant insertion device.

10. The interbody spacer according to claim 1, wherein the distal end portion includes a substantially contoured configuration.

11. The interbody spacer according to claim 10, wherein the top and bottom surfaces of the body portion approximate towards one another along the longitudinal axis adjacent the distal end portion.

12. The interbody spacer according to claim 1, wherein the top and bottom surfaces are substantially parallel.

13. The interbody spacer according to claim 1, wherein the top and bottom surfaces approximate towards one another in a direction transverse to the longitudinal axis.

14. The interbody spacer according to claim 1, wherein the sidewalls are closer together at an upper portion of the cavity and define a maximum distance from one another at a position between the top and bottom surfaces.

15. A method of performing spinal surgery, comprising:
preparing an intervertebral space between first and second vertebral bodies; and
advancing an interbody spacer in the intervertebral space, the interbody spacer including:
a body portion defining a longitudinal axis, the body portion including a distal end portion, a proximal end portion, opposed side surfaces that extend between the distal and proximal end portions, and top and bottom surfaces defining a vertical axis therethrough, at least one of the top and bottom surfaces having projections thereon configured and adapted to engage adjacent vertebral bodies, wherein the body portion includes a cavity defined through the top and bottom surfaces and bounded by the opposed side surfaces and the distal and proximal end portions, the cavity defining sidewalls being closer together proximate the top and bottom surfaces and being further apart at a center position between the top and bottom surfaces such that a center cross-section of the cavity defines a cross-sectional area that is greater than cross-sections disposed adjacent the top surface and the bottom surface, the sidewalls extending uninterrupted along a perimeter thereof, the cavity configured to retain biological material therein.

16. The method according to claim 15, further including packing the cavity with bone in-growth material.

17. The method according to claim 15, further including packing the cavity with drugs.

18. The method according to claim 15, wherein advancing the interbody spacer includes the interbody spacer having a cavity that includes undercuts defined therein, the undercuts defining convex sidewalls forming a portion of the sidewalls of the cavity.

19. The method according to claim 15, wherein advancing the interbody spacer includes the interbody spacer having a cavity that includes undercuts defined therein, the undercuts defining planar sidewalls forming a portion of the sidewalls of the cavity.

20. The method according to claim 15, wherein advancing the interbody spacer includes the interbody spacer having a plurality of substantially concentrically arranged ridges.

21. The method according to claim 20, wherein advancing the interbody spacer includes the plurality of substantially concentrically arranged ridges being a plurality of ring-shaped protrusions that define a generally saw-tooth pattern in a radial direction.

* * * * *

UNITED STATES PATENT AND TRADEMARK OFFICE
CERTIFICATE OF CORRECTION

PATENT NO. : 9,987,051 B2
APPLICATION NO. : 15/007523
DATED : June 5, 2018
INVENTOR(S) : Nunley et al.

Page 1 of 1

It is certified that error appears in the above-identified patent and that said Letters Patent is hereby corrected as shown below:

On the Title Page (72) Inventor reads:
Kaitlyn McClymont
Should read:
Kaitlin McClymont Signed and Sealed this
Twenty-fifth Day of September, 2018

Andrei Iancu
*Director of the United States Patent and Trademark Office*